United States Patent [19]

Credner et al.

[11] 4,092,417
[45] May 30, 1978

[54] THEOPHYLLINE SALTS OF 5-METHYLISOXAZOLE-3-CARBOXYLIC ACID

[75] Inventors: Karl Credner, Kaarst; Joachim Göring, Gronau; Günter Brenner, Grefarth; Manfred Tauscher, Gronau, Leine, all of Germany

[73] Assignee: Johann A. Wulfing, Germany

[21] Appl. No.: 748,507

[22] Filed: Dec. 8, 1976

[51] Int. Cl.² .................... A61K 31/52; C07D 473/08
[52] U.S. Cl. ...................................... 424/253; 544/269
[58] Field of Search ........................ 260/253; 424/253

[56] References Cited

U.S. PATENT DOCUMENTS

| | | | |
|---|---|---|---|
| 2,924,598 | 2/1960 | Bestian et al. | 260/253 |
| 3,801,578 | 4/1974 | Harsanyi et al. | 260/253 |
| 3,980,646 | 9/1976 | Brenner et al. | 424/253 |

*Primary Examiner*—Paul M. Coughlan, Jr.
*Attorney, Agent, or Firm*—Jacobs & Jacobs

[57] ABSTRACT

The salts of N-unsubstituted, N-monosubstituted and N,N-disubstituted 7-(3-amino-2-hydroxypropyl)theophylline and 5-methylisoxazole-3-carboxylic acid are hypolipidaemic agents. The compounds, of which the 7-[3-(N-methyl-N-2-hydroxyethyl)amino-2-hydroxypropyl]-theophylline salt of 5-methylisoxazole-3-carboxylic acid is a representative embodiment, are prepared by allowing the isoxazole acid and the amine to react.

37 Claims, No Drawings

THEOPHYLLINE SALTS OF 5-METHYLISOXAZOLE-3-CARBOXYLIC ACID

The present invention relates to salts of 5-methylisoxazole-3-carboxylic acid, to their preparation and to compositions containing them.

More specifically this invention provides salts of the formula (I):

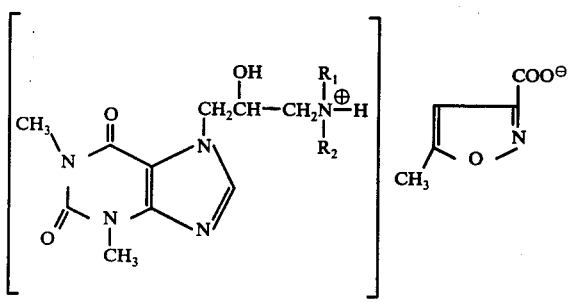

wherein $R_1$ and $R_2$ are each a hydrogen atom or an alkyl, hydroxyalkyl or alkoxyalkyl group of up to 6 carbon atoms or a cyclohexyl group.

Suitably $R_1$ and $R_2$ are alkyl groups of 1–4 carbon atoms or alkyl groups of 1–6 carbon atoms substituted by a hydroxyl, methoxyl, ethoxyl, propoxyl or butoxyl group.

Particularly suitable groups $R_2$ are the methyl, ethyl, 2-hydroxyethyl, 2-methoxyethyl groups.

A preferred group $R_1$ is the methyl group.

Particularly suitable groups $R_1$ are the methyl, ethyl, 2-hydroxyethyl, 2-methoxyethyl and 2-ethoxyethyl groups.

A preferred group $R_2$ is the 2-hydroxyethyl group.

From the foregoing it will be realized that a particularly suitable compound of the formula (I) is the 7-[3-(N-methyl-N-2-hydroxyethyl) amino-2-hydroxypropyl]theophylline salt of 5-methylisoxazole-3-carboxyic acid.

The compounds of the invention are produced by reacting of corresponding substituted 1,3 dimethyl xanthins of the formula (II):

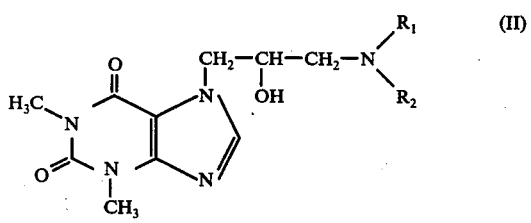

in which $R_1$ and $R_2$ are as defined in relation to formula (I) with 5-methylisoxazole-3-carboxylic acid Accordingly the present invention provides a pharmaceutical composition which comprises a compound of the formula (I) as hereinbefore defined and a pharmaceutically acceptable carrier therefore.

The compositions of this invention may be presented in forms suitable for oral or parenteral administration but orally administrable forms are preferred.

The compositions of this invention may be formulated in any convenient manner such as capsules, tablets or the like. The carriers used may be conventional bulking agents, disintegrants, lubricants, preservatives, or the like as will be well understood to the skilled formulation worker.

Unit dosage forms will generally contain from 0.5 to 20 mg, for example from 1 to 10 mg and may be administered 1 or more times daily, for example from 2 to 4 times daily so that the daily dose for a 70 kg adult will usually be in the range 2 to 50 mg. It has been pointed out by Gerritsen and Dulin (Excerpta Med. No. 74, 80, 1964) that isoxazole derivatives possess the capacity of lowering the free fatty acid level in plasma.

The reaction is suitably carried out at a temperature of 40° C to 100° C, preferably at the boiling temperature of the solvent.

The reaction is normally carried out in an organic solvent such as lower alcohols such as methanol, ethanol, isopropanol, the butanols optionally together with solvents such as acetic esters or water in small amounts.

Normally approximately equimolar quantities of the base and acid are used.

Normally the pure base and acid are used so that a product of acceptable purity may be obtained.

The compounds obtained of general formula I are preferably re-crystallised from a solvent such as lower alcohols such as methanol, ethanol, propanol, isopropanol or butanol, possibly in the presence of other solvents such as water, acetic acid, acetone or dioxane.

The compounds of the invention are distinguished by lipolysis-inhibiting and triglyceride-lowering activity. These properties permit the application of these compounds as medical agents for the treatment of hyperlipidaemas. A particularly favourable action is exhibited by the 7-[3-(N-methyl-N-2-hydroxyethyl)-amino-2-hydroxypropyl]theophylline salt of 5-methylisoxazole-3-carboxylic acid.

EXAMPLE 1

7-[3-(N-methyl-N-2-hydroxyethyl)-amino-2hydroxypropyl]-theophylline 5-methyl-isoxazole-3-carboxylate 62.2 g (0,2 mol) of 7-[3-(N-methyl-N-hydroxyethyl)-amino-2 hydroxypropyl]-theophylline (thin layer chromatographically pure) are dissolved in 200 ml. of absolute alcohol and to this solution at the boil with stirring, a saturated solution of 25.4 g (0.2 mol) of 5-methylisoxazole-3-carboxylic acid-3 (thin layer chromatographically pure) is added dropwise. After completed addition, the clear solution is allowed to cool at room temperature.

Colourless crystals separate out and are removed under suction. A further crystalline fraction is obtained from the mother liquor (obtained by suction under vacuum, by allowing it to stand in the refrigerator), which is combined with the first fraction and recrystallised from methanol with the addition of some isopropanol. Yield 72.1 g, m.p. 124.5°–125.5°.

[Analysis. Required C = 49.31%, H = 5.98%, N = 19.17%, O = 25.54%. Found C = 49.45%, H = 5.97%, N = 18.78%, O = 25.74%.]

EXAMPLES 2 TO 8

The further compounds of general formula I cited in Table I are produced according to the procedure of Example I.

| Number of Example | R₁ | R₂ | Melting point in 0° C Solvent for recrystallization. | Yield % of theory |
|---|---|---|---|---|
| | [As in formula (I)] | | | |
| 2 | CH₂—CH₂—CH₂—CH₃ | CH₂—CH₂—OH | 134.5–135.0 acetic acid ester/ethanol | 89 |
| 3 | CH₃ \| C—CH₃ \| CH₃ | CH₂—CH₂—OH | 146.5–147.5 acetic acid ester/ethanol | 66 |
| 4 | H | CH₂—CH₂—OCH₃ | 154.0–155.0 n-butanol/ethanol | 82 |
| 5 | H | CH₂—CH₂—O—(CH₂)₃—CH₃ | 137.0–138.0 acetic acid ester/ethanol | 89 |
| 6 | CH₂—CH₂—OH | CH₂—CH₂—OH | 148.0–149.0 ethanol | 75 |
| 7 | H | CH₂—CH₂—OH | 151.0–152.0 ethanol | 85 |
| 8 | CH₃ |  | 141.4–142.0 Dioxane/ether | 72 |

EXAMPLE 9

7-[3-(N-methyl-N-2-hydroxyethyl)-amino-2-hydroxypropyl]-theophylline 5-methyl-isoxazole-3-carboxylate was found to reduce the free fatty acid in the blood of 24 hr starved rats 1 hour post dose at doses as low as 1 mg/kg/po. In comparison 5-methyl-isoxazole-3-carboxylic acid had no significant effect at 5 mg/kg/po in this test system. The same compound of this invention was also found to lower triglycerides in the blood of 24 hr starved rats 1 hour post dose at doses as low as 10 mg/kg and also showed effects on serum cholesterol levels and sugar levels at 300 mg/kg/po.

What we claim is:

1. A salt of the formula:

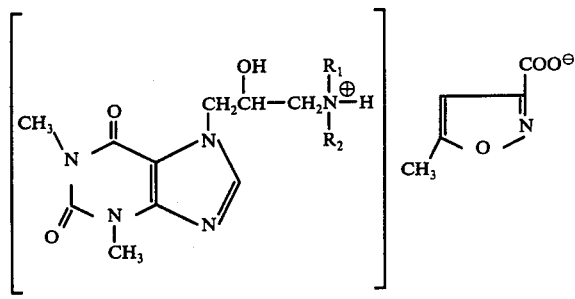

in which each of $R_1$ and $R_2$ is independently selected from the group consisting of hydrogen, alkyl of up to 6 carbon atoms, hydroxyalkyl of up to 6 carbon atoms, alkoxyalkyl of up to 6 carbon atoms and cyclohexyl.

2. A salt according to claim 1 wherein each of $R_1$ and $R_2$ is selected from the group consisting of methyl, ethyl, 2-hydroxyethyl, 2-methoxyethyl and 2-ethoxyethyl.

3. A salt according to claim 1 wherein $R_1$ is methyl.

4. A salt according to claim 1 wherein $R_2$ is 2-hydroxyethyl.

5. The salt according to claim 1 which is 7-[3-(N-methyl-N-2-hydroxyethyl)amino-2-hydroxypropyl]-theophylline 5-methylisoxazole-3-carboxylate.

6. The salt according to claim 1 which is 7-[3-(N-n-butyl-N-2-hydroxyethyl)amino-2-hydroxypropyl]-theophylline 5-methylisoxazole-3-carboxylate.

7. The salt according to claim 1 which is 7-[3-(N-t-butyl-N-2-hydroxyethyl)amino-2-hydroxypropyl]-theophylline 5-methylisoxazole-3-carboxylate.

8. The salt according to claim 1 which is 7-[3-(N-2-methoxyethyl)amino-2-hydroxypropyl]-theophylline 5-methylisoxazole-3-carboxylate.

9. The salt according to claim 1 which is 7-[3-(N-2-n-butoxyethyl)amino-2-hydroxypropyl]-theophylline 5-methylisoxazole-3-carboxylate.

10. The salt according to claim 1 which is 7-[3-(N,N-bis-2-hydroxyethyl)amino-2-hydroxypropyl]-theophylline 5-methylisoxazole-3-carboxylate.

11. The salt according to claim 1 which is 7-[3-(N-methyl-N-cyclohexyl)amino-2-hydroxypropyl]-theophylline 5-methylisoxazole-3-carboxylate.

12. A pharmaceutical composition for humans comprising a hypolipidaemically effective amount of a salt of the formula:

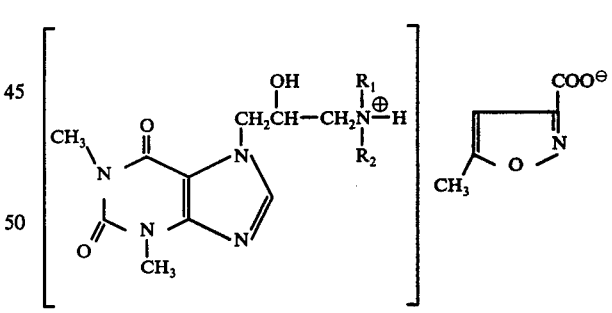

in which each of $R_1$ and $R_2$ is independently selected from the group consisting of hydrogen, alkyl of up to 6 carbon atoms, hydroxyalkyl of up to 6 carbon atoms, alkoxyalkyl of up to 6 carbon atoms and cyclohexyl, in combination with a pharmaceutically acceptable carrier.

13. A composition according to claim 12 wherein each of $R_1$ and $R_2$ is selected from the group consisting of methyl, ethyl, 2-hydroxyethyl, 2-methoxyethyl, and 2-ethoxyethyl.

14. A composition according to claim 12 wherein $R_1$ is methyl.

15. A composition according to claim 12 wherein $R_2$ is 2-hydroxyethyl.

16. A composition according to claim 12 wherein said salt is 7-[3-(N-methyl-N-2-hydroxyethyl)amino-2-hydroxypropyl]-theophylline 5-methylisoxazole-3-carboxylate.

17. A composition according to claim 12 wherein said salt is 7-[3-(N-n-butyl-N-2-hydroxyethyl)amino-2-hydroxypropyl]-theophylline 5-methylisoxazole-3-carboxylate.

18. A composition according to claim 12 wherein said salt is 7-[3-(N-t-butyl-N-2-hydroxyethyl)amino-2-hydroxypropyl]-theophylline 5-methylisoxazole-3-carboxylate.

19. A composition according to claim 12 wherein said salt is 7-[3-(N-2-methoxyethyl)amino-2-hydroxypropyl]-theophylline 5-methylisoxazole-3-carboxylate.

20. A composition according to claim 12 wherein said salt is 7-[3-(N-2-n-butoxyethyl)amino-2-hydroxypropyl]-theophylline 5-methylisoxazole-3-carboxylate.

21. A composition according to claim 12 wherein said salt is 7-[3-(N,N-bis-2-hydroxyethyl)amino-2-hydroxypropyl]-theophylline 5-methylisoxazole-3-carboxylate.

22. A composition according to claim 12 said salt is 7-[3-(N-methyl-N-cyclohexyl)amino-2-hydroxypropyl]-theophylline 5-methylisoxazole-3-carboxylate.

23. A composition according to claim 12 in oral administration form.

24. A composition according to claim 12 in parenteral administration form.

25. The method of treating hyperlipidaemia in a human which comprises administering thereto a hypolipidaemically effective amount of a salt of the formula:

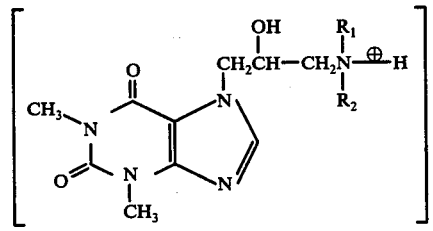

-continued

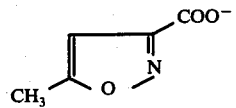

in which each of $R_1$ and $R_2$ is independently selected from the group consisting of hydrogen, alkyl of up to 6 carbon atoms, hydroxyalkyl of up to 6 carbon atoms, alkoxyalkyl of up to 6 carbon atoms and cyclohexyl.

26. A method according to claim 25 wherein each of $R_1$ and $R_2$ is selected from the group consisting of methyl, ethyl, 2-hydroxyethyl, 2-methoxyethyl, and 2-ethoxyethyl.

27. A method according to claim 25 wherein $R_1$ is methyl.

28. A method according to claim 25 wherein $R_2$ is 2-hydroxyethyl.

29. The method according to claim 25 wherein said salt is 7-[3-(N-methyl-N-2-hydroxyethyl)amino-2-hydroxypropyl]-theophylline 5-methylisoxazole-3-carboxylate.

30. The method according to claim 25 wherein said salt is 7-[3-(N-n-butyl-N-2-hydroxyethyl)amino-2-hydroxypropyl]-theophylline 5-methylisoxazole-3-carboxylate.

31. The method according to claim 25 wherein said salt is 7-[3-(N-t-butyl-N-2-hydroxyethyl)amino-2-hydroxypropyl]-theophylline 5-methylisoxazole-3-carboxylate.

32. The method according to claim 25 wherein said salt is 7-[3-(N-2-methoxyethyl)amino-2-hydroxypropyl]-theophylline 5-methylisoxazole-3-carboxylate.

33. The method according to claim 25 wherein said salt is 7-[3-(N-2-n-butoxyethyl)amino-2-hydroxypropyl]-theophylline 5-methylisoxazole-3-carboxylate.

34. The method according to claim 25 wherein said salt is 7-[3-(N,N-bis-2-hydroxyethyl)amino-2-hydroxypropyl]-theophylline 5-methylisoxazole-3-carboxylate.

35. The method according to claim 25 wherein said salt is 7-[3-(N-methyl-N-cyclohexyl)amino-2-hydroxypropyl]-theophylline 5-methylisoxazole-3-carboxylate.

36. A method according to claim 25 wherein the administration is oral.

37. A method according to claim 25 wherein the administration is parenteral.

* * * * *